(12) United States Patent
Sui et al.

(10) Patent No.: US 6,583,153 B2
(45) Date of Patent: Jun. 24, 2003

(54) 7-HETEROCYCLYL QUINOLINE AND THIENO[2,3-B]YRIDINE DERIVATIVES USEFUL AS ANTAGONISTS OF GONADOTROPIN RELEASING HORMONE

(75) Inventors: Zhihua Sui, Flemington, NJ (US); Mark Macielag, Branchburg, NJ (US); James C. Lanter, Flemington, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/992,785

(22) Filed: Nov. 14, 2001

(65) Prior Publication Data

US 2002/0123506 A1 Sep. 5, 2002

Related U.S. Application Data

(60) Provisional application No. 60/254,827, filed on Dec. 12, 2000.

(51) Int. Cl.[7] ............... A61K 31/4745; A61K 31/4355; C07D 471/04; C07D 405/04; C07D 409/04; A61P 15/00
(52) U.S. Cl. ................. 514/293; 514/312; 514/313; 514/267; 546/82; 546/83; 546/156; 546/159; 544/250
(58) Field of Search .................. 546/82, 83, 156, 546/159; 544/250; 514/293, 312, 267, 313

(56) References Cited

U.S. PATENT DOCUMENTS

| | | | |
|---|---|---|---|
| 5,140,009 A | | 8/1992 | Haviv et al. |
| 5,171,835 A | | 12/1992 | Janaky et al. |
| 5,807,869 A | * | 9/1998 | Furuya et al. ............... 514/312 |
| 6,015,789 A | | 1/2000 | Suzuki et al. |

FOREIGN PATENT DOCUMENTS

| | | |
|---|---|---|
| EP | 0679642 A1 | 11/1995 |
| JP | 61191698 | 4/1987 |
| WO | WO 95/28405 A1 | 10/1995 |
| WO | WO 95/29900 A1 | 11/1995 |
| WO | WO 96/38438 A1 | 12/1996 |
| WO | WO 97/14682 A1 | 4/1997 |
| WO | WO 97/14697 A1 | 4/1997 |
| WO | WO 97/21703 A1 | 6/1997 |
| WO | WO 97/21707 A1 | 6/1997 |
| WO | WO 97/41126 A1 | 11/1997 |
| WO | WO 97/44037 A1 | 11/1997 |
| WO | WO 97/44041 A1 | 11/1997 |
| WO | WO 97/44321 A1 | 11/1997 |
| WO | WO 97/44339 A | 11/1997 |

OTHER PUBLICATIONS

Bienstock et al., "Conformational Analysis of a Highly Potent Dicyclic Gonadotropin–Releasing Hormone Antagonist by Nuclear Magnetic Resonance and Molecular Dynamics", J. Med. Chem. 1993, 36, pp 3265–3273.

Burgus et al., Primary Structure of the Ovine Hypothalamic Luteinizing Hormone–Releasing Factor (LRF), Proc. Nat. Acad. Sci. USA, Jan. 1972, vol. 69, No. 1, pp 278–282.

Matsuo et al., Structure of the Porcine LH–and Fish–Releasing Hormone. I. The Proposed Amino Acid Sequence, Biochemical and Biophysical Research Communication, vol. 43, No. 6, 1971, pp 1334–1339.

PCT International Search Report, PCT Appln. No. PCT/US01/48119, dated Jun. 4, 2002, which corresponds to U.S. Appln. No. 09/992,785, filed Nov. 14, 2001.

* cited by examiner

*Primary Examiner*—Evelyn Mei Huang

(57) ABSTRACT

The present invention is directed to novel 7-heterocyclyl quinoline and thieno[2,3-b]pyridine derivatives of the general formula (I) or (II)

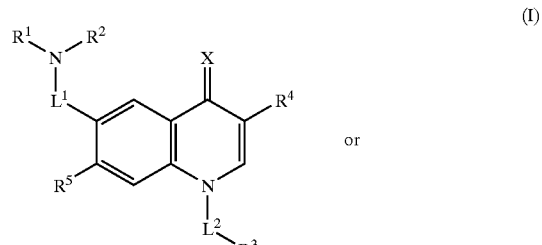

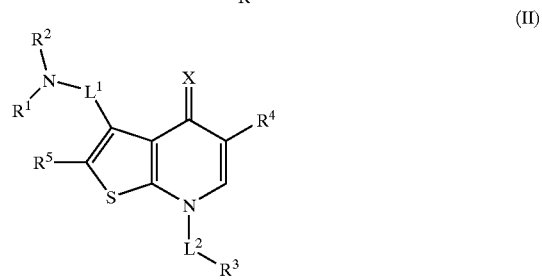

wherein all variables are as herein defined, pharmaceutical compositions containing them and their use in the treatment of disorders and conditions associated with gonadotropin releasing hormone (GnRH). The compounds of the invention are antagonists of GnRH, useful in the treatment of the infertility, prostate cancer, benign prostate hyperplasia (BPH) and as contraceptives.

12 Claims, No Drawings

7-HETEROCYCLYL QUINOLINE AND THIENO[2,3-B]YRIDINE DERIVATIVES USEFUL AS ANTAGONISTS OF GONADOTROPIN RELEASING HORMONE

This is a non-provisional of prior application Ser. No.: 60/254,827, filed Dec. 12, 2000.

FIELD OF THE INVENTION

The present invention is directed to novel 7-heterocyclyl quinoline and thieno[2,3-b]pyridine derivatives, pharmaceutical compositions containing them and their use in the treatment of disorders and conditions associated with gonadotropin releasing hormone (GnRH). The compounds of the invention are antagonists of GnRH, useful in the treatment of infertility, prostate cancer, benign prostate hyperplasia (BPH), and useful as contraceptives.

BACKGROUND OF THE INVENTION

Gonadotropin-releasing hormone (GnRH), also referred to as luteinizing hormone-releasing hormone (LHRH) is a linear decapeptide amide, pGlu-His-Trp-Ser-Tyr-Gly-Leu-Arg-Pro-Gly-$NH_2$, originally isolated from porcine (Matsuo, H., et. al., *Biochem. Biophys. Res. Commun.* 1972, 43,1334–1339) and ovine (Burgus, R., et. al., *PNAS*, USA, 1972, 69, 278–282) sources. GnRH plays a key role in the reproductive system. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both males and females, whereas FSH regulates spermatogenesis in males and follicular development in females.

GnRH-based therapies using peptidic GnRH agonists and antagonists have been shown effective in the treatment of conditions associated with LH/FSH release, such as endometriosis, uterine fibroids, polycystic ovarian disease, precocious puberty and some gonadal steroid-dependent neoplasia, particularly prostate cancer, breast cancer and ovarian cancer. GnRH agonists and antagonists are also useful in the treatment of fertility and as a contraceptive in both males and females.

Although the compounds of the present invention are useful primarily for the treatment of disorders and conditions associated with the reproductive system, they may also be useful for the treatment of other GnRH mediated disorders and conditions including pituitary gonadotrope adenomas, sleep disorders, benign prostate hyperplasia, and prostate cancer.

Peptide-like GnRH antagonists are known, for example, derivatives of straight-chain peptides (U.S. Pat. Nos. 5,140, 009 and 517,835), cyclic hexapeptide derivatives (Japanese Patent Application Laid-open No. 61(1986)-191698), and bicyclic peptide derivatives (J. Med. Chem. 1993, 36, 3265). However, due to a lack of bioavailability, these compounds are limited to intravenous and subcutaneous administration.

Recently, small molecule, non-peptide GnRH antagonists have been disclosed. Kato, et al., in EP0679642 disclose isochroman derivatives which have gonadotropin releasing hormone receptor antagonizing activity, as well as calcium-antagonizing and monoamine-uptake inhibiting activities.

Ohkawa et al., in WO96/38438 disclose tricyclic diazepine derivatives which have gonadotropin releasing hormone receptor antagonist activity. Ohkawa et al., in WO95/29900 disclose condensed heterocyclic compounds which have GnRH receptor antagonistic action and/or an action of improving sleep disturbances.

Furuya et al., in WO97/14682 disclose quinolone derivatives as GnRH antagonists, useful as prophylactic or therapeutic agents for the prevention or treatment of sex hormone dependent disease.

Goulet et al., in WO97/44037 and in WO97/44041, Goulet et al., in WO97/44321 and Goulet et al., in WO97/44339 disclose non-peptide antagonists of GnRH useful for the treatment of a variety of sex-hormone related conditions in men and women. Goulet et al., in WO97/21703 and in WO97/21707 disclose non-peptide antagonists of GnRH useful for the treatment of a variety of sex-hormone related conditions in men and women.

Furuya et al., in WO95/28405 disclose bicyclic thiophene derivatives with gonadotropin releasing hormone receptor antagonizing activity. Furuya et al., in WO97/41126 disclose 4,7-dihydro-4-oxothieno[2,3-b]pyridine derivatives having GnRH antagonistic activity. Furuya, et al., in WO97/14697 disclose thieno[2,3-b]pyridine derivatives as GnRH antagonists.

SUMMARY OF THE INVENTION

The present invention is directed to a compound of formula (I) or (II):

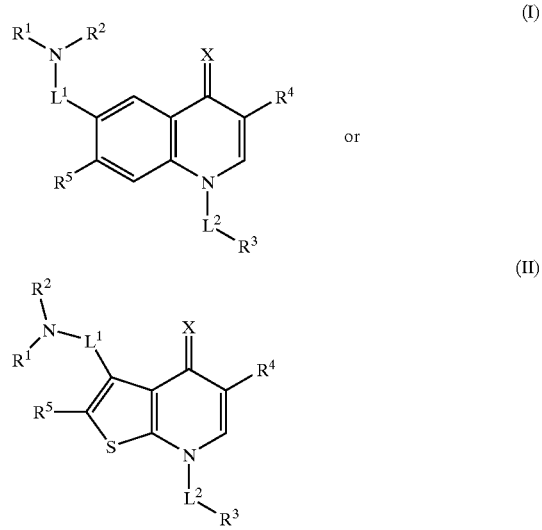

wherein $L^1$ is selected from the group consisting of $CH_2$, $CH(CH_3)$ and $C(CH_3)_2$;

$R^1$ and $R^2$ are independently selected from the group consisting of alkyl, cycloalkyl, aryl, aralkyl, heteroaryl and heterocycloalkyl; wherein the aryl, heteroaryl or heterocycloalkyl group is optionally substituted with one or more substituents independently selected from halogen, alkyl, alkoxy, nitro, $NH_2$, NH(alkyl), N(alkyl)$_2$, —C(O)-alkyl, —C(O)-aryl or —C(O)-cycloalkyl;

X is selected from the group consisting of O, S and $NR^A$; where $R^A$ is selected from hydrogen, alkyl, aryl or aralkyl;

$R^4$ is selected from the group consisting of —C(O)—$R^B$, —C(O)O—$R^B$, —C(O)$NH_2$, —C(O)—$NHR^B$, —C(O)—N($R^B$)$_2$, and —C(O)$NHNH_2$;

wherein $R^B$ is selected from the group consisting of alkyl, aryl, aralkyl and cycloalkyl;

alternatively X is N and is taken together with R⁴ to form a ring structure selected from the group consisting of pyrazolyl, dihydropyrazolyl, isoxazolinyl and dihydropyrimidinyl; wherein the ring structure is optionally substituted with one or more R$^C$;

wherein each R$^C$ is independently selected from the group consisting of oxo, alkyl, alkoxy, amino, alkylamino, dialkylamino, aryl, —O-aryl, aralkyl and —O-aralkyl;

L² is selected from the group consisting of alkyl;

R³ is selected from the group consisting of alkyl, cycloalkyl, aryl, aralkyl, heteroaryl and heterocycloalkyl; wherein the cycloalkyl, aryl, aralkyl, heteroaryl or heterocycloalkyl group is optionally substituted with one or more substituents independently selected from halogen, alkyl, alkoxy, nitro, NH₂, NH(alkyl), N(alkyl)₂, cyano or sulfonamido;

R⁵ is selected from the group consisting of halogen, cycloalkyl, aryl, aralkyl, heteroaryl or heterocycloalkyl; wherein the cycloalkyl, aryl, aralkyl, heteroaryl or heterocycloalkyl group is optionally substituted with one or more substituents selected from halogen, alkyl, alkoxy, nitro, NH₂, NH(alkyl), N(alkyl)₂, cyano or sulfonamido;

provided that when X is O, then R⁵ is selected from the group consisting of heteroaryl or heterocycloalkyl; wherein the heteroaryl or heterocycloalkyl group is optionally substituted with one or more substituents selected from halogen, alkyl, alkoxy, nitro, NH₂, NH(alkyl), N(alkyl)₂, cyano or sulfonamido;

and pharmaceutically acceptable salts, esters and prodrugs thereof.

In an aspect of the present invention is the compound 4,7-dihydro-2-(4-methoxyphenyl)-7-[(2-methoxyphenyl)methyl]-3-[[methyl(phenylmethyl)amino]methyl]-4-oxothieno[2,3-b]pyridine-5-carboxylic acid hydrazide, and pharmaceutically acceptable salts, esters and prodrugs thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders or diseases which respond to antagonism of GnRH, in a subject in need thereof comprising administering to the subject a therapeutically effective amount of any of the compounds or pharmaceutical compositions described above.

An example of the invention is a method for treating infertility, prostate cancer or benign prostate hyperplasia (BPH), in a subject in need thereof comprising administering to the subject an effective amount of any of the compounds or pharmaceutical compositions described above.

A further example of the invention is a method of female or male contraception, in a subject in need thereof comprising administering to the subject a therapeutically effective amount of any of the compounds or pharmaceutical compositions described above.

Yet another example of the invention is the use of any of the compounds described herein in the preparation of a medicament for treating: (a) infertility, (b) prostate cancer, (c) benign prostate hyperplasia (BPH) or for (d) contraception, in a subject in need thereof.

DETAILED DESCRIPTION OF THE INVENTION

The present invention is directed to a compound of formula (I) or (I):

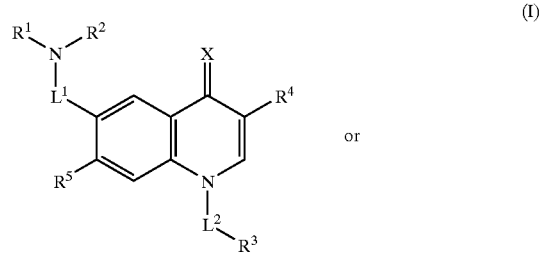

(I)

or

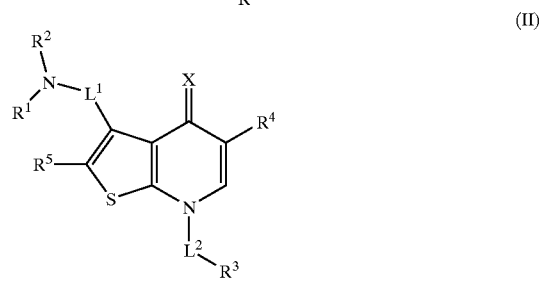

(II)

wherein L¹, R¹, R², X, R⁴, L², R³ and R⁵ are as previously described, useful in the treatment of disorders or diseases which respond to antagonism of the GnRH such as infertility, prostate cancer, benign prostate hyperplasia (BPH), and the like. The compounds of the present invention are further useful as contraceptives.

In one embodiment of the present invention are compounds of the formula (I) wherein L¹ is CH₂;

R¹ and R² are independently selected from the group consisting of lower alkyl, cycloalkyl, aryl, aralkyl, heteroaryl and heterocycloalkyl; wherein the aryl, aralkyl, heteroaryl or heterocycloalkyl may be optionally substituted with one to two substituents independently selected from halogen, lower alkyl, lower alkoxy, nitro, NH₂, NH(lower alkyl) or N(lower alkyl)₂;

X is O;

R⁴ is selected from the group consisting of —C(O)O-alkyl, —C(O)O-aryl and —C(O)NHNH₂;

alternatively X is N and is taken together with R⁴ to form a ring structure selected from the group consisting of pyrazolyl, pyrazolinyl, dihydropyridyl and dihydropyrimidyl, wherein the ring structure is optionally substituted with one to two substituents independently selected from oxo, lower alkyl, lower alkoxy, aryl, —O-aryl, aralkyl or —O-aralkyl;

L² is selected from the group consisting of lower alkyl;

R³ is selected from the group consisting of aryl; wherein the aryl group is optionally substituted with one to two substituents independently selected from halogen, lower alkyl, lower alkoxy, nitro, NH₂, NH(lower alkyl), N(lower alkyl)₂, cyano or sulfonamido;

R⁵ is selected from the group consisting of halogen, cycloalkyl, aryl, aralkyl, heteroaryl, and heterocycloalkyl wherein the cycloalkyl, aryl, aralkyl, heteroaryl or heterocycloalkyl is optionally substituted with one to two substituents independently selected from halogen, lower alkyl, lower alkoxy, nitro, NH₂, NH(lower alkyl), N(lower alkyl)₂, cyano or sulfonamido;

provided that when X is O, then $R^5$ is selected from the group consisting of heteroaryl or heterocycloalkyl; wherein the heteroaryl or heterocyloalkyl group is optionally substituted with one to two substituents selected from halogen, lower alkyl, lower alkoxy, nitro, $NH_2$, NH(lower alkyl), N(lower alkyl)$_2$, cyano or sulfonamido;

and pharmaceutically acceptable salts, esters and prodrugs thereof.

In another embodiment of the present invention are compounds of the formula (I) or (II) wherein X is S and $R^5$ is selected from the group consisting of heteroaryl or heterocycloalkyl; wherein the heteroaryl or heterocycloalkyl group is optionally substituted with one or more substituents selected from halogen, alkyl, alkoxy, nitro, $NH_2$, NH(alkyl), N(alkyl)$_2$, cyano or sulfonamido;

In a further embodiment of the present invention are compounds of the formula (I) or (II) wherein X is $NR^A$ or alternatively X is N and is taken together with $R^4$ to form a ring structure selected from the group consisting of pyrazolyl, dihydropyrazolyl, isoxazolinyl and dihydropyrimidinyl; wherein the ring structure is optionally substituted with one or more $R^C$, wherein $R^C$ is as defined above.

In a particularly preferred embodiment of the present invention are compounds of the formula (I) and (II) as listed in Tables 1 and 2.

TABLE I

| ID # | X | $R^4$ | $R^5$ | Mol. Wt. (M$^{+1}$) |
|---|---|---|---|---|
| 1 | O | —C(O)OCH$_2$CH$_3$ | 3-thienyl | 559 |
| 2 | O | —C(O)OCH$_2$CH$_3$ | 2-benzofuryl | 593 |
| 3 |   |   | bromo | 524 |
| 4 |   |   | 2-benzofuryl | 561 |
| 5 |   |   | 2-benzofuryl | 651 |

TABLE I-continued

| ID # | X | $R^4$ | $R^5$ | Mol. Wt. (M$^{+1}$) |
|---|---|---|---|---|
| 6 |   |   | 2-benzofuryl | 589 |

TABLE II

| ID # | X | $R^4$ | Mol Wt (M$^{+1}$) |
|---|---|---|---|
| 7 | O | —C(O)—NH—NH$_2$ | 569 |
| 8 |   |   | 551 |

As used herein, "halogen" shall mean chlorine, bromine, fluorine and iodine.

As used herein, the term "alkyl" whether used alone or as part of a substituent group, includes straight and branched chains comprising one to ten carbon atoms. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1–6 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "lower" when used with alkoxy means an oxygen ether radical of the above described straight or branched carbon chain alkyl group wherein the alkyl is of 1–6 carbon atoms.

As used herein, unless otherwise noted, "aryl" shall refer to carbocyclic aromatic groups such as phenyl, naphthyl, and the like.

As used herein, unless otherwise noted, "aralkyl" shall mean any lower alkyl group substituted with an aryl group such as phenyl, naphthyl and the like. For example, benzyl, phenylethyl, phenylpropyl, naphthylmethyl, and the like.

As used herein, unless otherwise noted, "cycloalkyl" shall mean any three to eight membered, monocyclic, saturated, carbocyclic ring structure including cyclopropyl, cyclobutyl, cyclopentyl, cyclohexyl, cycloheptyl and cylcooctyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated, partially unsaturated or partially aromatic ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl and 2,3-dihydrobenzofuryl and the like.

When a particular group is "substituted" (e.g., cycloalkyl, aryl, aralkyl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenylalkylaminocarbonylalkyl" substituent refers to a group of the formula

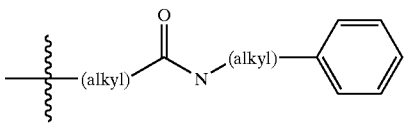

Names for chemical entities of the present invention may be generated using nomenclature rules known in the art or may alternatively be generated using commercial chemical naming software, for example ACD/Index Name (Advanced Chemistry Development, Inc., Toronto, Ontario)

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly the Schemes and Examples, are as follows:

| | |
|---|---|
| αMEM = | Minimum Essential Medium |
| DCM = | Dichloromethane |
| DIPEA = | Diisopropylethylamine |
| DMF = | N,N-Dimethylformamide |
| DME = | Dimethoxyethane |
| DMSO = | Dimethylsulfoxide |
| $Et_3N$ = | Triethylamine |
| EtOAc = | Ethyl Acetate |
| LHMDS = | Lithium hexamethyldisilazide |
| MeOH = | Methanol |
| NBS = | 1-bromo-2,5-pyrrolidinedione |
| Ph = | Phenyl |
| RT or rt = | Room temperature |
| TEA = | Triethylamine |
| THF = | Tetrahydrofuran |

Compounds of the general formula (I) wherein X is O, may be prepared according to the process outlined in Scheme 1.

Scheme 1

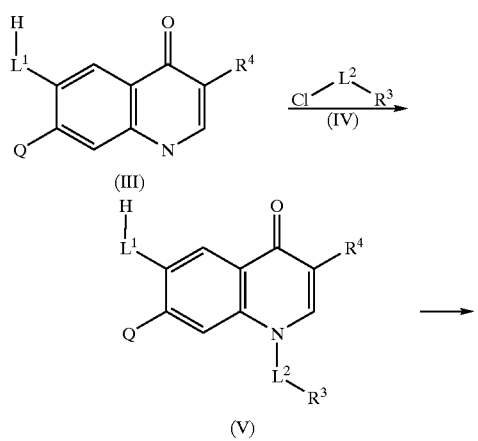

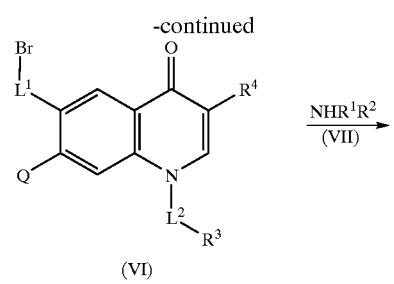

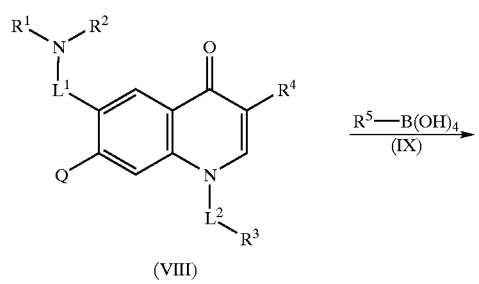

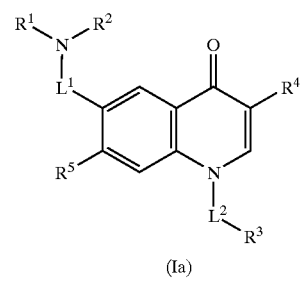

More particularly, a compound of formula (III), a known compound or compound prepared by known methods, wherein Q is bromo or iodo, is reacted with a suitably substituted compound of formula (IV), in the presence of a base such as potassium carbonate, TEA, NaOH, NaH, DIPEA, and the like, in an organic solvent such as THF, DMF, DCM, and the like, to yield the corresponding compound of formula (V).

The compound of formula (V) is reacted with a brominating agent such as 70% NBS, and the like, in an organic solvent such as THF, DMF, DCM, and the like, to yield the corresponding compound of formula (VI).

The compound of formula (VI) is reacted with a suitably substituted amine of formula (VII), in the presence of a base such as TEA, DIPEA, and the like, in an organic solvent such as THF, DMF, and the like, to yield the corresponding compound of formula (VIII).

The compound of formula (VIII) is reacted with a suitably substituted boronic acid of formula (IX), in the presence of a catalyst such as palladium tetrakis(triphenylphosphine) ($Pd(PPh_3)_4$), and the like, in the presence of a base such as $NaCO_3$, NaOH, and the like, in an organic solvent such as THF, DMF, dioxane, and the like, optionally in a mixture with water, to yield the corresponding compound of formula (Ia).

Compounds of formula (I) wherein X is S may be prepared according to the process outlined in Scheme 2.

Scheme 2

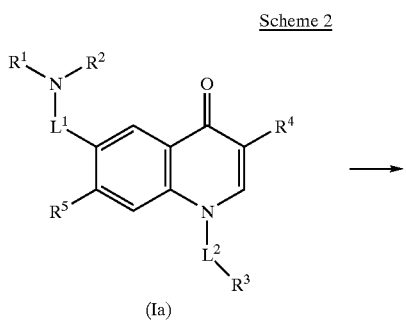

(Ia)

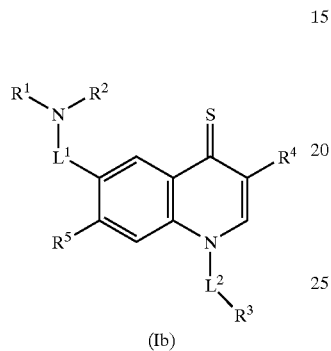

(Ib)

Specifically, a suitably substituted compound of formula (Ia), prepared as in Scheme 1, is reacted with a sulfonating agent such as $P_4S_{10}$, Lawesson's reagent, and the like, in an organic solvent such as pyridine, toluene, xylene, and the like, at an elevated temperature in the range of about 60–140° C., to yield the corresponding compound of formula (Ib).

Compounds of formula (I) wherein X is N and is taken together with $R^4$ to form

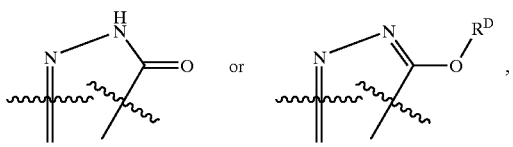

wherein $R^D$ is selected from the group consisting of alkyl, aryl and aralkyl, may be prepared according to the process outlined in Scheme 3.

Scheme 3

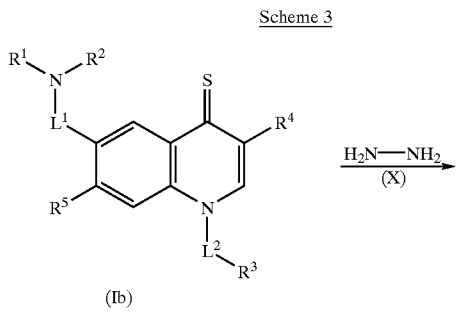

(Ib)

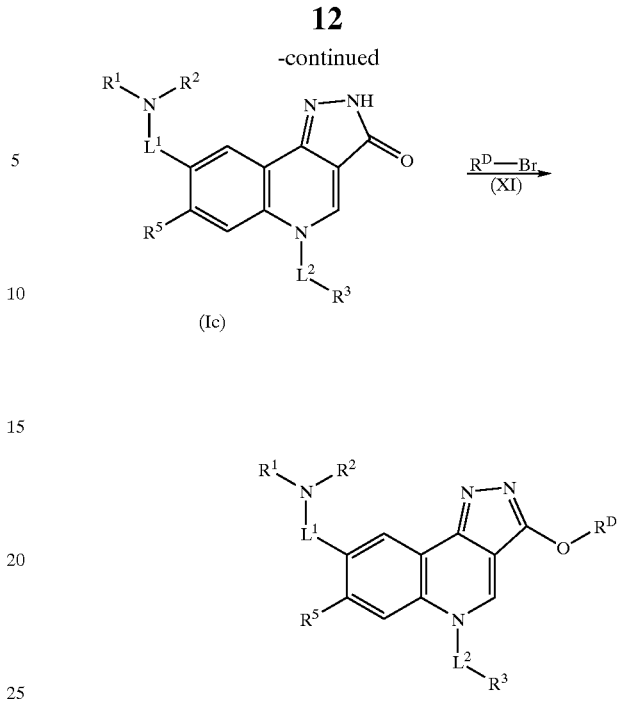

(Ic)

(Id)

More particularly, a suitably substituted compound of formula (Ib), prepared as in Scheme 2, is reacted with a compound of formula (X), in an organic solvent such as DMF, DMSO, and the like, at an elevated temperature in the range of about 80–110° C., to yield the corresponding compound of formula (Ic).

The compound of formula (Ic) is optionally further reacted with a compound of formula (XI), wherein $R^D$ is selected from the group consisting of alkyl, aryl and aralkyl, in the presence of a strong base such as LHMDS, NaH, potassium t-butoxide, and the like, to yield the corresponding compound of formula (Id).

Alternatively, the compound of formula (Ic) may be further reacted according to known methods to introduce one or more substituents on the pyrazolyl group.

Compounds of formula (I) wherein X is $NR^A$ may be prepared according to the process outlined in Scheme 4.

Scheme 4

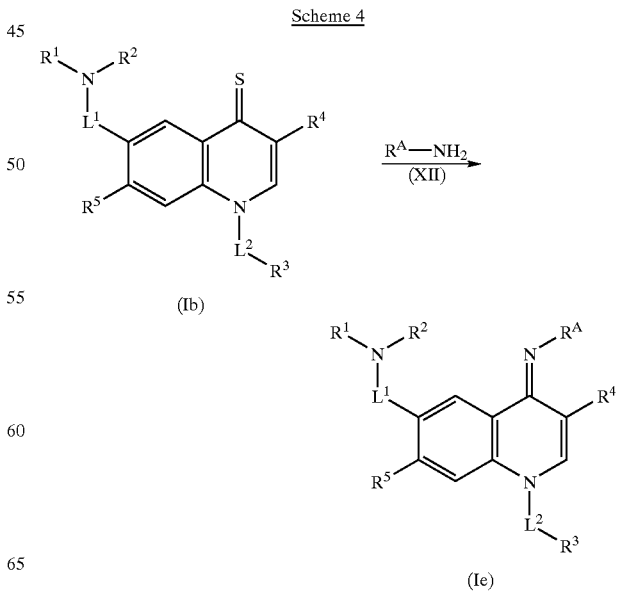

(Ib)

(Ie)

More particularly, a suitably substituted compound of formula (Ib), prepared as in Scheme 2, is reacted with a suitably substituted amine of formula (XII), in an organic solvent such as DMF, DMSO, and the like, preferably at an elevated temperature in the range of about 60–120° C., to yield the corresponding compound of formula (Ie).

Compounds of formula (I) wherein X is N and is taken together with $R^4$ to form a ring structure selected from the group consisting of dihydropyrazolyl, isoxazolinyl and dihydropyrimidinyl may be prepared by methods known to those skilled in the art.

For example, compounds of formula (I) wherein X is N and is taken together with $R^4$ to form dihydropyrazolyl

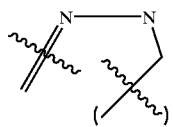

may be prepared by reacting a suitably substituted compound of formula (Ia), wherein X is O and $R^4$ is an ester of the formula —$CO_2R^B$, prepared as in Scheme 1, with a suitable reducing agent, to yield the corresponding compound wherein $R^4$ is an aldehyde of the formula —C(O)H, subsequently reacting the $R^4$ aldehyde with benzylcarbazate to yield the corresponding compound wherein $R^4$ is hydrazone (—CHNNH—C(O)O-benzyl), reducing the $R^4$ hydrazone with hydrogen gas, in the presence of a catalyst such as palladium hydroxide, to yield the corresponding compound wherein $R^4$ is hydrazine (—$CH_2NHNH_2$), and then treating the $R^4$ hydrazine with a dehydration reagent such as $P_2O_5$, at an elevated temperature to yield the corresponding dihydropyrazole substituted compound of formula (I).

Compounds of formula (I) wherein X is N and is taken together with $R^4$ to form isoxazolinyl

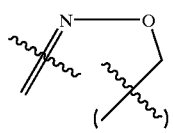

may be prepared by subjecting a suitably substituted compound of formula (Ia), wherein X is O and $R^4$ is an ester of the formula —$CO_2R^B$, prepared as in Scheme 1, to saponification to convert the $R^4$ ester group to the corresponding carboxy group (—$CO_2H$) and then treating the $R^4$ carboxy group with a suitable reducing agent, to yield the corresponding compound wherein $R^4$ is an alcohol of the formula —$CH_2OH$, converting the X is O carbonyl group to the corresponding X is S thiocarbonyl group, converting the thiocarbonyl group to the corresponding hydroxyamine where X is N—OH, and then affecting ring closure of the X hydroxyamine and $R^4$ alcohol with a dehydrating agent such as $P_2O_5$, at an elevated temperature to yield the corresponding isoxazolinyl substituted compound of formula (I).

Compounds of formula (I) wherein X is N and is taken together with $R^4$ to form dihydropyrimidinyl

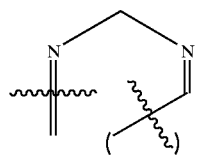

or oxo-substituted dihydropyrimidinyl

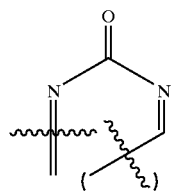

may be prepared by reacting a suitably substituted compound of formula (Ia), wherein $R^4$ is an ester of the formula —$CO_2R^B$, prepared as in Scheme 1, with urea, thiourea, guanidine or a suitably substituted alkyl or aryl amidine, in an organic solvent, at an elevated temperature to yield the corresponding oxo-substituted dihydropyrimidinyl

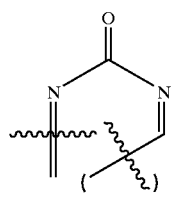

thio-substituted dihydropyrimidinyl

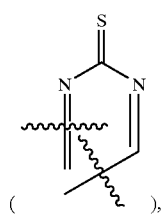

imino-substituted dihydropyrimidinyl

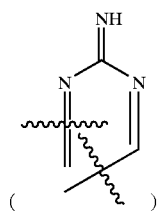

or alkyl or aryl substituted dihydropyrimidinyl

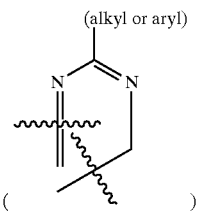
(alkyl or aryl)

substituted compound of formula (I). The oxo-substituted dihydropyrimidinyl substituted compound of formula (I) may be further optionally, alkylated according to the process described in Scheme 3, to yield the corresponding dihydropyrimidinyl substituted compound of formula (I). Similarly, the thio- or imino-substituted dihydropyrimidinyl substituted compound of formula (I) may be further, optionally reacted according to known methods to displace the thio group (=S) or modify the imino group (=NH), respectively.

Compounds of formula (II), wherein $R^4$ is —C(O)O—$R^6$, X is S or X is N and is taken together with $R^4$ to form

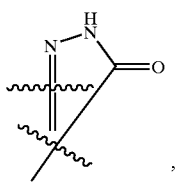
, may be prepared according to the process outlined in Scheme 5.

Scheme 5

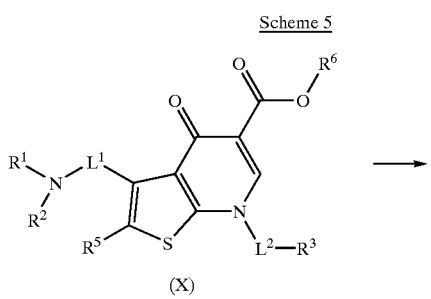
(X)

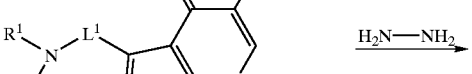
(IIa)

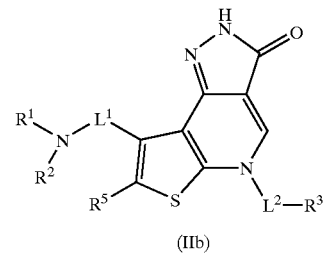
(IIb)

More particularly, a compound of formula (X), a known compound or compound prepared by known methods, is reacted with a sulfonating agent such as $P_4S_{10}$, Lawesson's Reagent, and the like, in the presence of an organic base such as pyridine, TEA, Hünig's base (DIEA), and the like, at an elevated temperature in the range of about 60–120° C., preferably at about reflux temperature, to yield the corresponding compound of formula (IIa).

The compound of formula (IIa) may be optionally further reacted with $H_2N$—$NH_2$, in an organic solvent such as DMF, DMSO, and the like, at an elevated temperature in the range of about 80–110° C., to yield the corresponding compound of formula (IIb).

The compound of formula (IIb) may be further, optionally reacted according to known methods to introduce one or more substituents on the pyrazolyl group.

Compounds of formula (II) wherein X is N and taken together with $R^4$ to form a ring selected from the group consisting of dihydropyrazolyl, isoxazolinyl and dihydropyrimidinyl, may be similarly prepared according to the processes described above, with appropriate substitution of a compound of formula (X) for the compound of formula (Ia).

Compounds of formula (II) wherein X is selected from the group consisting of O, S and $NR^A$, may be prepared from the corresponding compound of formula (X), by methods known to those skilled in the art.

For example, compounds of formula (II) wherein X is O and $R^4$ is other than —C(O)O$R^6$ may be prepared by converting the $R^4$ ester group on a suitably substituted compound of formula (X) to the corresponding $R^4$ carboxy group and then using known quinolone chemistry to convert the $R^4$ carboxy group to the desired $R^4$ functionality.

Compounds of formula (II) wherein X is S and $R^4$ is other than —C(O)O$R^6$, may similarly be prepared by converting the —C(O)O$R^6$ ester on the compound of formula (X) to the desired $R^4$ group as described above and then converting the X is O, (carbonyl group) to the corresponding X is S (thiocarbonyl group) by reacting with a sulfonating agent, as described in Scheme 5.

Compounds of formula (II) wherein X is $NR^A$ and $R^4$ is other than —C(O)O$R^6$, may similarly be prepared by converting the —C(O)O$R^6$ ester on the compound of formula (X) to the desired $R^4$ group as described above and then converting the X is O (carbonyl group) to the corresponding X is $NR^A$ (amine group) by reacting with a suitably substituted amine, as described in Scheme 4.

The following Examples are set forth to aid in the understanding of the invention, and are not intended and should not be construed to limit in any way the invention set forth in the claims which follow thereafter.

EXAMPLE 1

7-Bromo-6-bromomethyl-1-(2,6-difluorobenzyl)-1, 4-dihydro-4-oxoquinoline-3-carboxylic acid ethylester A mixture of 7-bromo-1-(2,6-difluorobenzyl)-1,4-dihydro-6-methyl-4-oxoquinoline-3-carboxylic acid ethyl ester (3.5 g, 8 mmol), prepared according to the procedure outlined in PCT application WO97/14682, Reference Example 3, NBS (1.5 g, 8.4 mmol) and 2,2'-azobisisobutyronitrile (AIBN, 100 mg) in DCM (200 mL) was stirred at reflux for 4 h. Additional NBS (750 mg) was added and the mixture was refluxed for 4 h. Column chromatography (hexanes:ethyl acetate=3:7) yielded the product as a white solid.

Yield: 2.95 g (72%)

m.p. 184–187° C.;

$^1$H NMR (CDCl$_3$), δ1.41 (t, J=8 Hz, 3 H), 4.40 (q, J=8 Hz, 2 H), 4.66 (s, 2 H), 5.36 (s, 2H), 7.03 (m, 2 H), 7.39 (m, 1 H), 7.92 (s, 1 H), 8.54 (s, 1 H), 8.68 (ds, 1 H);

MS (m/z): 514 (MH$^+$).

EXAMPLE 2

6-(N-Benzyl-N-methylaminomethyl)-7-bromo-1-(2, 6-difluorobenzyl)-1,4-dihydro-4-oxoquinoline-3-carboxylic acid ethylester A mixture of 7-bromo-6-bromomethyl-1-(2,6-difluorobenzyl)-1,4-dihydro-4-oxoquinoline-3-carboxylic acid ethyl ester (110 mg, 0.21 mmol), methylbenzylamine (31 mg, 0.26 mmol) in DIPEA (0.045 mL) and DMF (15 mL) was stirred at room temperature for 16 h. Ethyl acetate and water were added. The organic phase was separated and washed with water, dried with MgSO$_4$. The solvent was evaporated and the residue dried under vacuum to yield the product as a white solid.

Yield: 120 mg (100%)

$^1$H NMR (CDCl$_3$), δ1.41 (t, J=8 Hz, 3 H), 2.17 (s, 3 H), 3.62 (s, 2 H), 3.67 (s, 2 H), 4.40 (q, J=8 Hz, 2 H), 5.36 (s, 2H), 7.03 (m, 2 H), 7.25–7.39 (m, 6 H), 7.88 (s, 1 H), 8.59 (s, 1 H), 8.67 (ds, 1 H);

MS (m/z): 555 (MH$^+$).

EXAMPLE 3

6-(N-Benzyl-N-methylaminomethyl)-7-(benzofuran-2-yl)-1-(2,6-difluorobenzyl)-1,4-dihydro-4-oxoquinoline-3-carboxylic acid ethylester Compound #2

A mixture of 7-bromo-6-bromomethyl-1-(2,6-difluorobenzyl)-1,4-dihydro-4-oxoquinoline-3-carboxylic acid ethyl ester (278 mg, 0.5 mmol), benzofuran-2-boronic acid (97 mg, 0.6 mmol), tetrakis(triphenylphosphine) palladium(0) (69 mg, 0.06 mmol) and 2M sodium carbonate (414 mg, 3 mmol) in DME (20 mL) was heated at reflux for 16 h. Ethyl acetate and water were added. The organic phase was separated and washed with water and dried with MgSO$_4$. Column chromatography (ethyl acetate) yielded the product as a yellow solid.

Yield: 55 mg (19%)

$^1$H NMR (CDCl$_3$), δ1.44 (t, J=8 Hz, 3 H), 2.17 (s, 3 H), 3.63 (s, 2 H), 3.90 (s, 2 H), 4.42 (q, J=8 Hz, 2 H), 5.49 (s, 2H), 7.00 (m, 2 H), 7.22–7.81 (m, 11 H), 8.23 (s, 1 H), 8.62 (s, 1 H), 8.76 (ds, 1 H);

MS (m/z): 593 (MH$^+$).

EXAMPLE 4

2,5-dihydro-7-(4-methoxyphenyl)-5-[(2-methoxyphenyl)methyl]-8-[[methyl(phenylmethyl)amino]methyl]-3H-pyrazolo[3,4-d]thieno[2,3-b]pyridin-3-one Compound #8

To a solution of 4,7-dihydro-2-(4-methoxy-phenyl)-7-[(2-methoxyphenyl)methyl]-3-[[methyl(phenylmethyl)amino]methyl]-4-oxo-thieno[2,3-b]pyridine-5-carboxylic acid, ethyl ester (prepared according to the procedure described by Furuya, S, et al., in PCT Application WO95/28405), (387 mg, 0.66 mmol) in pyridine (3 mL) was added P$_4$S$_{10}$. The reaction flask was flushed with argon and stirred at reflux for 5 hours. The solvent was removed and the product purified by flash chromatography to yield the corresponding thiocarbonyl.

The thiocarbonyl (118 mg, 0.19 mmol) was dissolved in dry DMF (0.25 mL) and treated with hydrazine monohydrate (0.02 mL, 0.42 mmol). The resulting solution was heated to 80° C. for 2 hours, the mixture was cooled and purified by flash chromatography (0–10% MeOH/CHCl$_3$). The product was converted to its hydrochloride salt by treating with HCl to yield the product as a yellow powder.

Yield: 7.5 mg

MS (m/z) 551 (MH$^+$).

EXAMPLE 5

2,5-Dihydro-7-(benzofuran-2-yl)-8-[[methyl(phenylmethyl)amino]methyl]-5-[(2,6-difluorophenyl)methyl]-3H-pyrazolo[4,3-c]quinolin-3-one Compound #4

To a solution of 7-(benzofuran-2-yl)-8-[[methyl(phenylmethyl)-amino]-methyl]-5-[(2,6-difluorophenyl)methyl]-3-quinolinecarboxylic acid ethyl ester, (500 mg, 0.84 mmol) in pyridine (5 mL) was added P$_4$S$_{10}$ (240 mg, 0.65 eq). The reaction flask was flushed with argon and stirred at reflux for 2 hours, cooled to 100° C. and poured into water (100 mL). The product was extracted into chloroform, dried (MgSO$_4$) and concentrated to yield a red-brown solid.

The solid (337 mg, 0.55 mmol) was dissolved in dry DMF (5 mL) and treated with hydrazine monohydrate (60 mg, 1.1 mmol). The resulting mixture was warmed to 100° C. for 3 hours, the mixture was cooled and poured onto water. The resulting yellow precipitate was collected by filtration and dried to yield the product.

Yield: 149 mg $^1$H NMR (CDCl$_3$) δ2.09 (s, 3H), 3.57 (s, 2H), 3.86 (s, 2H), 5.84 (s, 2H), 7.18–7.49 (m, 12H), 7.66–7.77 (m, 2H), 8.16 (s, 1H), 8.33 (s, 1H), 8.95 (s, 1H).

EXAMPLE 6

7-(Benzofuran-2-yl)-3-[(phenylmethyl)oxy]-5-[(2,6-difluorophenyl)methyl]-8-[[methyl(phenylmethyl)amino]methyl]-5H-pyrazolo[4,3-c]quinoline Compound #5

A solution of 2,5-dihydro-7-(benzofuran-2-yl)-8-[[methyl(phenylmethyl)amino]methyl]-5-[(2,6-difluorophenyl)

methyl]-3H-pyrazolo[4,3-c]quinolin-3-one (120 mg, 0.21 mmol) in dry DMF (5 mL) was treated with a solution of lithium hexamethyldisilazide (0.25 mL, 0.25 mol, 1.0 M) in tetrahydrofuran (THF). Benzyl bromide (40 mg, 0.22 mmol) was introduced via syringe and the mixture was stirred overnight. One equivalent hydrochloric acid in ether was added and the solvent evaporated to yield the corresponding hydrochloride salt product as a yellow solid.

Yield: 47 mg $^1$H NMR (CDCl$_3$) δ2.08 (s, 3H), 3.55 (s, 2H), 3.87 (s, 2H), 5.13 (s, 2H), 5.88 (s, 2H), 7.12–7.51 (m, 16 H), 7.66–7.70 (m, 2H), 8.16 (s, 1H), 8.37 (s, 1H), 9.10 (s,1H).

EXAMPLE 7

6-(N-Benzyl-N-methylaminomethyl)-7-(thien-3-yl)-1-(2,6-difluorobenzyl)-1,4-dihydro-4-oxoquinoline-3-carboxylic acid ethyl ester Compound #1

Following the procedure described in Example 3, the compound prepared in Example 2 (6-(N-Benzyl-N-methylaminomethyl)-7-bromo-1-(2,6-difluorobenzyl)-1,4-dihydro-4-oxoquinoline-3-carboxylic acid ethylester) (150 mg, 0.27 mmol) was reacted with thiophene-3-boronic acid (38.4 mg, 0.30 mmol), to yield the product as a yellow solid.

Yield: 48 mg

MS(m/z) 559 (MH$^+$).

EXAMPLE 8

2,5-Dihydro-7-bromo-8-[[methyl(phenylmethyl)amino]methyl]-5-[(2,6-difluorophenyl)methyl]-3H-pyrazolo[4,3-c]quinolin-3-one Compound #3

Following the procedure described in Example 4, 6-(N-benzyl-N-methylaminomethyl)-7-bromo-1-(2,6-difluorobenzyl)-1,4-dihydro-4-oxoquinoline-3-carboxylic acid ethyl ester (0.6 g, 1.1 mmol) was converted to the title compound and isolated as the corresponding hydrochloride salt, as a yellow powder.

Yield: 0.15 g

MS (m/z) 524 (MH$^+$).

EXAMPLE 9

7-(Benzofuran-2-yl)-3-ethoxy-5-[(2,6-difluorophenyl)methyl]-8-[[methyl(phenylmethyl)amino]methyl]-5H-pyrazolo[4,3-c]quinoline HCl Compound #6

Following the procedure described in Example 6. 2,5-dihydro-7-(benzofuran-2-yl)-8-[[methyl(phenylmethyl)amino]methyl]-5-[(2,6-difluorophenyl)methyl]-3H-pyrazolo[4,3-c]quinolin-3-one (0.05 g, 0.09 mmol) was reacted with ethyl iodide (0.018 g, 0.116 mmol) to yield the title compound, which was isolated as its corresponding hydrochloride salt, as a yellow powder.

Yield: 0.05 g

MS (m/z) 589 (MH$^+$).

EXAMPLE 10

4,7-Dihydro-2-(4-methoxyphenyl)-7-[(2-methoxyphenyl)methyl]-3-[[methyl(phenylmethyl)amino]methyl]-4-oxo-thieno[2,3-b]pyridine-5-carboxylic acid, hydrazide bis-hydrochloride Compound #7

To a solution of 4,7-dihydro-2-(4-methoxyphenyl)-7-[(2-methoxyphenyl)methyl]-3-[[methyl(phenylmethyl)amino] methyl]-4-oxo-thieno[2,3-b]pyridine-5-carboxylic acid, ethyl ester (57 mg, 0.097 mmol) in ethyl alcohol (2 mL) was added hydrazine (0.030 mL, 0.096 mmol). The mixture was heated to reflux for 6 hours and concentrated in vacuo. Trituration of the residue with diethyl ether and collection of the solid by precipitation yielded the product as a pale yellow solid.

Yield: 38 mg

MS (m/z) 569 (MH$^+$).

EXAMPLE 11

GnRH Receptor Binding Assay

A homogenate prepared from an equal mixture of female and male rat pituitaries was used as the source of the membrane-bound GnRH receptor. The receptor was allowed to interact in solution with [$^{125}$I]-histrelin alone or in combination with a competitive ligand (the compound being tested). The bound radiolabeled ligand was separated from the free (unbound) radiolabeled ligand by filtration through glass filter mats using a 96-well plate harvesting system (Tomtec Mach II 96). In the absence of a competitive ligand, a maximum amount of radiolabeled ligand is bound to the receptor and trapped by the glass filter mats. When an unlabelled ligand that can compete for the receptor site is present, the amount of radiolabeled ligand bound to the receptor and trapped on the filter mat is proportionally reduced depending on the concentration of the competitor and on the strength of the competitor's affinity for the receptor. The amount of receptor-bound [$^{125}$I]-histrelin on the filter mat was determined using a Wallac Betaplate™ Liquid Scintillation Counter. Binding was determined as follows:

| | |
|---|---|
| NSB | Non-specific binding |
| B$_0$ | maximum concentration of compound |
| Average NSB: | (NSB1 + NSB2)/2 |
| Average B$_0$: | (B$_0$1 + B$_0$2)/2 |
| Corrected B$_0$: | Average B$_0$–Average NSB |

% inhibition of Corrected B$_0$ (or maximum response) was calculated as follows:

$$\% \text{ Inhibition} = \frac{100 - [((\text{Actual counts per minute} - \text{Average } NSB)}{\text{Corrected } B_0) * 100]}$$

EXAMPLE 12

LUCIFERASE Assay FOR GnRH

Hek 293 cells with the GnRHR gene were transfected with the hCG promoter and the luciferase reporter system. On day 1, the cells were plated at a density of 80,000 cells per well on a Poly-D-lysine pre-coated 96 well plate. The plates were incubated at 37° C. for 24 hours. On day 2, the spent media was decanted and replaced with fresh media. Test compounds, standard and controls were added to individual wells. All the dilutions were done in 7.5% DMSO/αMEM media. The assay was run in both agonist and antagonist format. For the antagonist format, the assay measurements were run against a standard of 0.6 nM Histrelin. On day 3, the levels of luciferase production were measured in a chemiluminescence assay using Enhanced Luciferase Assay Kit. The results were expressed as % Inhibition using the following formula:

| | |
|---|---|
| RLU | Relative Light Units, a measure of chemiluminescence |
| Agonist | [RLU value(test compound)-(Background/0.6 nM Histrelin)-Background] * 100 |
| Antagonist | (1-[(RLU value-(Background/0.6 nM Histrelin)-Background) * 100]) |

The calculated percentages were plotted on a graph using Graph Pad Prizm and the $IC_{50}/EC_{50}$ values determined.

EXAMPLE 13

Primary Pituitary Cell Culture Assay

Male rats (between immature and adult) were sacrificed and the anterior pituitaries were collected from them. The pituitaries were dissociated and the cells were plated at a concentration of $0.33 \times 10^6$ cells/well on day 1. On day 3 the media on the cells was flushed and replaced with fresh media. The test compound was then added to the plated cells at a concentration ranging from 1 nM to 1000 nM. The plates were incubated at 37° C. at 5% $CO_2$ for 2 days. On Day 5 the media was flushed again and replaced with fresh media. To the plates were then added test compound and 1 nM GnRH. The cells were incubated for 4 hours, the media was collected by centrifuging the plates at 1200 rpm Sorvall RT7 for 10 minutes, 900 μL of supernatant was pipetted from each well and dispensed to a 96 well plate. The deep well plates were covered and stored at 20° C. for a day. The plates are then evaluated by ELISA (a radioimmunoassay system) to determine the concentration of lutenizing hormone in the media. The assay was repeated at varying concentrations of the test compounds to determine $IC_{50}$ values. The $IC_{50}$ value is defined as the concentration of test compound at which 50% inhibition was achieved.

Following the procedures set forth above, selected compounds of the present invention were tested, with results as listed in Table 3.

TABLE 3

| | Biological Activity | | |
|---|---|---|---|
| ID # | Binding, $IC_{50}$ (B % @ 30 μM) | Luciferase Assay $IC_{50}$ (μM) | Pituitary Cell Assay $IC_{50}$ (μM) |
| 1 | 32 μM | 10 (antagonist) | |
| 2 | — | 3.26 (antagonist) | 2.43 |
| 3 | 16 | | |
| 4 | 1 | | |
| 5 | 5 | | |
| 6 | 5 | | |
| 7 | 1.6 | | 1.48 |
| 8 | 30 | | |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of the formula (I)

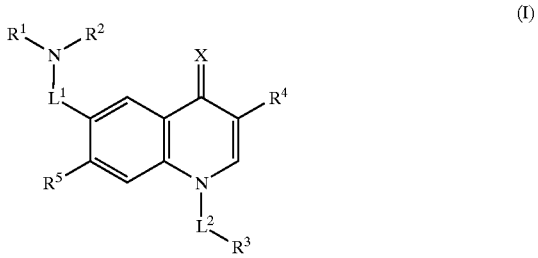

wherein $L^1$ is selected from the group consisting of $CH_2$, $CH(CH_3)$ and $C(CH_3)_2$;

$R^1$ and $R^2$ are independently selected from the group consisting of alkyl, cycloalkyl, aryl, aralkyl, heteroaryl and heterocycloalkyl; wherein the aryl, heteroaryl or heterocycloalkyl group is optionally substituted with one or more substituents independently selected from halogen, alkyl, alkoxy, nitro, $NH_2$, NH(alkyl), N(alkyl)$_2$, —C(O)-alkyl, —C(O)-aryl or —C(O)-cycloalkyl;

X is selected from the group consisting of O, S and $NR^A$; where $R^A$ is selected from hydrogen, alkyl, aryl or aralkyl;

$R^4$ is selected from the group consisting of —C(O)—$R^B$, —C(O)O—$R^B$, —C(O)$NH_2$, —C(O)—$NHR^B$, —C(O)—N($R^B$)$_2$, and —C(O)$NHNH_2$;

wherein $R^B$ is selected from the group consisting of alkyl, aryl, aralkyl and cycloalkyl;

alternatively X is N and is taken together with $R^4$ to form a ring structure selected from the group consisting of pyrazolyl, dihydropyrazolyl, isoxazolinyl and dihydropyrimidinyl; wherein the ring structure is optionally substituted with one or more $R^C$;

wherein each $R^C$ is independently selected from the group consisting of oxo, alkyl, alkoxy, amino, alkylamino, dialkylamino, aryl, —O-aryl, aralkyl and —O-aralkyl;

$L^2$ is selected from the group consisting of alkyl;

$R^3$ is selected from the group consisting of alkyl, cycloalkyl, aryl, aralkyl, heteroaryl and heterocycloalkyl; wherein the cycloalkyl, aryl, aralkyl, heteroaryl or heterocycloalkyl group is optionally substituted with one or more substituents independently selected from halogen, alkyl, alkoxy, nitro, $NH_2$, NH(alkyl), N(alkyl)$_2$, cyano or sulfonamido;

$R^5$ is selected from the group consisting of halogen, cycloalkyl, aryl, aralkyl, heteroaryl or heterocycloalkyl; wherein the cycloalkyl, aryl, aralkyl, heteroaryl or heterocycloalkyl group is optionally substituted with one or more substituents selected from halogen, alkyl, alkoxy, nitro, $NH_2$, NH(alkyl), N(alkyl);$_2$, cyano or sulfonamido;

provided that when X is O, then $R^5$ is selected from the group consisting of heteroaryl or heterocycloalkyl; wherein the heteroaryl or heterocycloalkyl group is optionally substituted with one or more substituents selected from halogen, alkyl, alkoxy, nitro, $NH_2$, NH(alkyl), N(alkyl)$_2$, cyano or sulfonamido;

and pharmaceutically acceptable salts, esters and prodrugs thereof.

2. A compound as in claim 1 wherein

L$^1$ is CH$_2$;

R$^1$ and R$^2$ are independently selected from the group consisting of lower alkyl, cycloalkyl, aryl, aralkyl, heteroaryl and heterocycloalkyl; wherein the aryl, aralkyl, heteroaryl or heterocycloalkyl may be optionally substituted with one to two substituents independently selected from halogen, lower alkyl, lower alkoxy, nitro, NH$_2$, NH(lower alkyl) or N(lower alkyl)$_2$;

X is O;

R$^4$ is selected from the group consisting of —C(O)O-alkyl, —C(O)O-aryl and —C(O)NHNH$_2$;

alternatively X is N and is taken together with R$^4$ to form a ring structure selected from the group consisting of pyrazolyl, pyrazolinyl, dihydropyridyl and dihydropyrimidyl, wherein the ring structure is optionally substituted with one to two substituents independently selected from oxo, lower alkyl, lower alkoxy, aryl, —O-aryl, aralkyl or —O-aralkyl;

L$^2$ is selected from the group consisting of lower alkyl;

R$^3$ is selected from the group consisting of aryl; wherein the aryl group is optionally substituted with one to two substituents independently selected from halogen, lower alkyl, lower alkoxy, nitro, NH$_2$, NH(lower alkyl), N(lower alkyl)$_2$, cyano or sulfonamido;

R$^5$ is selected from the group consisting of halogen, cycloalkyl, aryl, aralkyl, heteroaryl, and heterocycloalkyl wherein the cycloalkyl, aryl, aralkyl, heteroaryl or heterocycloalkyl is optionally substituted with one to two substituents independently selected from halogen, lower alkyl, lower alkoxy, nitro, NH$_2$, NH(lower alkyl), N(lower alkyl)$_2$, cyano or sulfonamido;

provided that when X is O, then R$^5$ is selected from the group consisting of heteroaryl or heterocycloalkyl; wherein the heteroaryl or heterocyloalkyl group is optionally substituted with one to two substituents selected from halogen, lower alkyl, lower alkoxy, nitro, NH$_2$, NH(lower alkyl), N(lower alkyl)$_2$, cyano or sulfonamido;

and pharmaceutically acceptable salts, esters and pro-drugs thereof.

3. A compound as in claim 1 wherein X is NR$^A$ or X is N and is taken together with R$^4$ to form a ring structure selected from the group consisting of pyrazolyl, dihydropyrazolyl, isoxazolinyl and dihydropyrimidinyl; wherein the ring structure is optionally substituted with one or more R$^C$; wherein each R$^C$ is independently selected from selected the group consisting of oxo, alkyl, alkoxy, amino, alkylamino, dialkylamino, aryl, —O-aryl, aralkyl and —O-aralkyl; and pharmaceutically acceptable salts, esters and pro-drugs thereof.

4. A compound as in claim 2 wherein

L$^1$ is CH$_2$;

R$^1$ is selected from the group consisting of lower alkyl;

R$^2$ is selected from the group consisting of aralkyl;

X is O;

R$^4$ is selected from the group consisting of —C(O)O-(lower alkyl);

alternatively, X is taken together with R$^4$ to form a group selected from

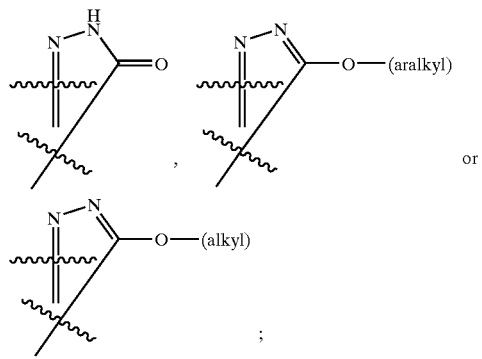

L$^2$ is selected from the group consisting of lower alkyl;

R$^3$ is selected from the group consisting of phenyl and substituted phenyl, wherein the substituents on the phenyl are one to two independently selected from halogen;

R$^5$ is selected from the group consisting of halogen and heteroaryl;

provided that when X is O, R$^5$ is heteroaryl;

and pharmaceutically acceptable salts, esters and pro-drugs thereof.

5. A compound as in claim 4 wherein

L$^1$ is CH$_2$;

R$^1$ is methyl;

R$^2$ is benzyl;

X is O;

R$^4$ is —C(O)O—CH$_2$CH$_3$;

alternatively, X is taken together with R$^4$ to form a group selected from

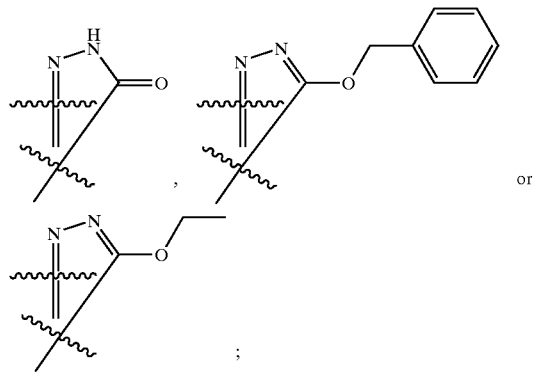

L$^2$ is CH$_2$;

R$^3$ is 2,6-di-fluorophenyl;

R$^5$ is selected from the group consisting of bromo, 3-theinyl and 2-benzofuryl; provided that when X is O, R$^5$ is selected from 3-theinyl and 2-benzofuryl;

and pharmaceutically acceptable salts, esters and pro-drugs thereof.

6. A compound as in claim 5 selected from the group consisting of

1-[(2,6-difluorophenyl)methyl]-1,4-dihydro-6-[[methyl (phenylmethyl)amino]methyl]-4-oxo-7-(3-thienyl)-3-quinolinecarboxylic acid ethyl ester;

7-(2-benzofuranyl)-1-[(2,6-difluorophenyl)methyl]-1,4-dihydro-6-[[methyl(phenylmethyl)amino]methyl]-4-oxo-3-quinolinecarboxylic acid, ethyl ester;

7-bromo-5-[(2,6-difluorophenyl)methyl]-2,5-dihydro-8-[[methyl(phenylmethyl)amino]methyl]-3H-pyrazolo[4,3-c]quinolin-3-one;

7-(2-benzofuranyl)-5-[(2,6-difluorophenyl)methyl]-2,5-dihydro-8-[[methyl(phenylmethyl)amino]methyl]-3H-pyrazolo[4,3-c]quinolin-3-one;

7-(benzofuran-2-yl)-5-[(2,6-difluorophenyl)methyl]-3-[(phenylmethyl)oxy]-8-[[methyl(phenylmethyl)amino]methyl]-5H-pyrazolo[4,3-c]quinoline 7-(benzofuran-2-yl)-5-[(2,6-difluorophenyl)methyl]-3-ethoxy-8-[[methyl(phenylmethyl)amino]methyl]-5H-pyrazolo[4,3-c]quinoline;

and pharmaceutically acceptable salts, esters and prodrugs thereof.

7. A pharmaceutical composition comprising a pharmaceutically acceptable carrier and a compound of claim 1.

8. A pharmaceutical composition made by mixing a compound of claim 1 and a pharmaceutically acceptable carrier.

9. A process for making a pharmaceutical composition comprising mixing a compound of claim 1 and a pharmaceutically acceptable carrier.

10. A method of treating a disorder or disease which respond to antagonism of the GnRH in a subject in need thereof comprising administering to the subject a GnRH antagonizing effective amount of the composition of claim 7 wherein the disorder or disease is selected from the group consisting of infertility, prostate cancer and benign prostate hyperplasia (BPH).

11. A method of contraception in a subject in need thereof comprising administering to the subject a GnRh antagonizing effective amount of the compound of claim 1.

12. A method of treating a condition selected from the group consisting of the infertility, prostate cancer and benign prostate hyperplasia (BPH) in a subject in need thereof comprising administering to the subject a GnRH antagonizing effective amount of the compound of claim 1.

* * * * *